United States Patent
Colak Atan et al.

(10) Patent No.: US 11,964,073 B2
(45) Date of Patent: Apr. 23, 2024

(54) CURED ADHESIVE COMPOSITIONS AND METHOD OF MAKING

(71) Applicant: 3M INNOVATIVE PROPERTIES COMPANY, St. Paul, MN (US)

(72) Inventors: Semra Colak Atan, Saint Louis Park, MN (US); Grant W. Fahnhorst, Minneapolis, MN (US); Val Vossen, Minneapolis, MN (US); Jerald K. Rasmussen, Woodville, WI (US); James P. DiZio, St. Paul, MN (US); Abigail J. Halmes, Roseville, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 18/248,431

(22) PCT Filed: Oct. 11, 2021

(86) PCT No.: PCT/IB2021/059298
§ 371 (c)(1),
(2) Date: Apr. 10, 2023

(87) PCT Pub. No.: WO2022/090842
PCT Pub. Date: May 5, 2022

(65) Prior Publication Data
US 2023/0347011 A1 Nov. 2, 2023

Related U.S. Application Data

(60) Provisional application No. 63/198,569, filed on Oct. 28, 2020.

(51) Int. Cl.
*A61L 24/04* (2006.01)
*C08G 73/02* (2006.01)

(52) U.S. Cl.
CPC .......... *A61L 24/046* (2013.01); *C08G 73/024* (2013.01); *C08G 2170/00* (2013.01)

(58) Field of Classification Search
CPC .. A61L 24/046; C08G 73/024; C08G 2170/00
See application file for complete search history.

(56) References Cited

U.S. PATENT DOCUMENTS

| 4,767,619 | A | 8/1988 | Murray |
| 5,916,585 | A | 6/1999 | Cook et al. |
| 10,196,548 | B2 | 2/2019 | Rasmussen et al. |
| 10,808,078 | B2 | 10/2020 | Kou et al. |
| 2012/0271025 | A1 | 10/2012 | Hays et al. |
| 2018/0355230 | A1* | 12/2018 | Rasmussen ............ C09J 133/14 |
| 2020/0332423 | A1* | 10/2020 | Dhawan ................. C23F 11/10 |

FOREIGN PATENT DOCUMENTS

| CA | 3136427 A1 | 10/2020 |
| CN | 103025778 A | 4/2013 |
| CN | 108699241 A | 10/2018 |
| JP | 2011-529117 A | 12/2011 |
| JP | 2020-111746 A | 7/2020 |
| WO | 2011/138458 A1 | 11/2011 |
| WO | 2020/214196 A1 | 10/2020 |

OTHER PUBLICATIONS

Holycross, "Comprehensive NMR Studies of the Structures and Properties of PEI Polymers", 2013, Macromolecules, vol. 46, No. 17, pp. 6891-6897.
International Search Report received for PCT International Application No. PCT/IB2021/059298, dated Mar. 2, 2022, 4 pages.

* cited by examiner

*Primary Examiner* — Daniel H Lee
(74) *Attorney, Agent, or Firm* — Jean A. Lown

(57) ABSTRACT

A multiple-part curable composition, a cured composition formed by combining and reacting the multiple-part curable composition, and a method of providing a cured composition are described. The multiple-part curable composition contains at least a part A and a part B. Part A contains an oxalamido-containing compound while part B contains a derivatized polyethylene imine. The cured composition is an adhesive that is suitable for use as a tissue adhesive.

20 Claims, No Drawings

CURED ADHESIVE COMPOSITIONS AND METHOD OF MAKING

CROSS REFERENCE TO RELATED APPLICATIONS

This application is a national stage filing under 35 U.S.C. 371 of PCT/IB2021/059298, filed Oct. 11, 2021, which claims the benefit of U.S. Provisional Patent Application No. 63/198,569, filed Oct. 28, 2020, the disclosure of which is incorporated by reference in its/their entirety herein.

BACKGROUND

Staples and sutures are commonly used for wound closure in operating or emergency room settings. While staples and sutures may be necessary for closure of large and/or high-tension wounds, there is increased interest in using tissue adhesives alone or in combination with inner or deep sutures for the closure of smaller wounds. Tissue adhesives can offer several advantages over mechanical devices such as staples and sutures. For example, tissue adhesives can be less painful, can lead to a better cosmetic outcome, can provide a microbial barrier against further infections, and can be applied rapidly.

Some existing tissue adhesives contain cyanoacrylates that have a low viscosity and that can seep into unwanted locations either inside or outside the wound bed. Further, the cyanoacrylates tend to be cytotoxic, tend to cure slowly, and can cause skin burns due to their excessive curing exotherms. Still further, the cured adhesives tend to be stiff and usually cannot be used in areas where flexibility is needed.

SUMMARY

A multiple-part curable composition, a cured composition prepared from the multiple-part curable composition, and a method of providing a cured composition are described. The cured composition is an adhesive and is suitable for use as a tissue adhesive. The multi-part curable compositions usually have desirable attributes such as high viscosity and rapid curing with low curing exotherms when combined. The cured compositions tend to be flexible and biocompatible while providing a combination of good mechanical and adhesive strength.

In a first aspect, a multiple-part curable composition is provided. The multiple-part curable composition includes a part A comprising an oxalamido-containing compound and a part B comprising a derivatized polyethylene imine. The oxalamido-containing compound in part A has a molecular weight of at least 250 grams/mole and has at least two oxalamido groups of formula —NR$^2$—(CO)—(CO)—OR$^1$ wherein R$^1$ is a hydrocarbyl and wherein R$^2$ is hydrogen or hydrocarbyl. The derivatized polyethylene imine in Part B contains a reaction product of a polyethylene imine with a glycidyl ether, wherein the derivatized polyethylene imine contains monomeric units of Formula (VI) along with other monomeric units.

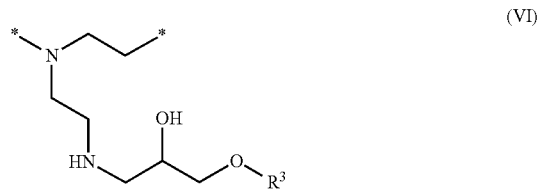

(VI)

In Formula (VI), R$^3$ is an alkyl having at least 4 carbon atoms, an aryl, an aralkyl, or an alkaryl and each asterisk (*) is an attachment site to another monomeric unit (i.e., any monomeric unit in the polymeric chain).

In a second aspect, a cured composition is provided that comprises a cured reaction product of the multiple-part curable composition described in the first aspect. The cured composition is typically an adhesive that is suitable for use as a tissue adhesive.

In a third aspect, a method of providing a curable composition is described. The method includes preparing or obtaining a part A composition as well as preparing or obtaining a part B composition. The part A composition comprises an oxalamido-containing compound that has a molecular weight of at least 250 grams/mole and that has at least two oxalamido groups of formula —NR$^2$—(CO)—(CO)—OR$^1$, wherein R$^1$ is a hydrocarbyl and wherein R$^2$ is hydrogen or hydrocarbyl. The part B composition comprises a derivatized polyethylene imine comprising a reaction product of a polyethylene imine with a glycidyl ether. The derivatized polyethylene imine contains monomeric units of Formula (VI) along with other monomeric units.

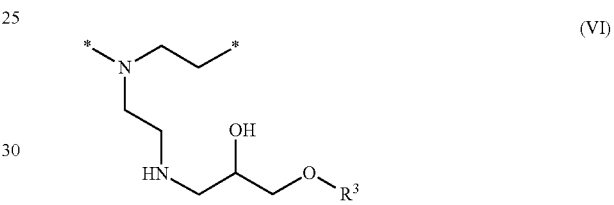

(VI)

In Formula (VI), the group R$^3$ is an alkyl having at least 4 carbon atoms, an aryl, an aralkyl, or an alkaryl. Each asterisk (*) is an attachment site to another monomeric unit (i.e., any monomeric unit in the polymeric chain) of the derivatized polyethylene imine. The method further includes combining part A with part B to form a reaction mixture and then curing the reaction mixture to form the cured composition that is an adhesive.

As used herein, the terms "a", "an", and "the" are used interchangeably with the term "at least one".

The term "and/or" such as in the expression X and/or Z means X alone, Z alone, or both X and Z.

The term "alkyl" refers to a monovalent group that is a radical of an alkane and includes groups that are linear, branched, cyclic, bicyclic, or a combination thereof. Unless otherwise indicated, the alkyl groups typically contain 1 to 30 carbon atoms. In some embodiments, the alkyl groups contain 1 to 20 carbon atoms, 1 to 10 carbon atoms, 1 to 6 carbon atoms, 1 to 4 carbon atoms, or 1 to 3 carbon atoms. Branched and cyclic alkyl groups have at least 3 carbon atoms and bicyclic alkyl groups typically have at least 7 carbon atoms. Example alkyl groups include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, norbornyl, and the like.

The term "alkylene" refers to a divalent group that is a di-radical of an alkane and includes groups that are linear, branched, cyclic, bicyclic, or a combination thereof. Unless otherwise indicated, the alkylene group typically has 1 to 30 carbon atoms. In some embodiments, the alkylene group has 1 to 20 carbon atoms, 1 to 10 carbon atoms, 1 to 6 carbon atoms, or 1 to 4 carbon atoms. Branched and cyclic alkylene groups have at least 3 carbon atoms and bicyclic alkylene groups typically have at least 7 carbon atoms. Example alkylene groups include methylene, ethylene, 1,3-propylene, 1,2-propylene, 1,4-butylene, 1,4-cyclohexylene, and 1,4-cyclohexyldimethylene.

The term "alkenyl" refers to a monovalent group that is a radical of an alkene and includes groups that are linear, branched, cyclic, bicyclic, or a combination thereof. Unless otherwise indicated, the alkenyl group typically has 2 to 30 carbon atoms, 2 to 20 carbon atoms, 2 to 10 carbon atoms, 2 to 6 carbon atoms, or 2 to 4 carbon atoms. Branched and cyclic alkenyl groups have at least 3 carbon atoms and bicyclic alkylene groups typically have at least 7 carbon atoms. There is one of more carbon-carbon double bonds.

The term "alkenylene" refers to a divalent group that is a di-radical of an alkene and includes groups that are linear, branched, cyclic, bicyclic, or a combination thereof. Unless otherwise indicated, the alkenylene group typically has 2 to 30 carbon atoms, 2 to 20 carbon atoms, 2 to 10 carbon atoms, 2 to 6 carbon atoms, or 2 to 4 carbon atoms. Branched and cyclic alkenylene groups have at least 3 carbon atoms and bicyclic alkenylene groups typically have at least 7 carbon atoms. There is one of more carbon-carbon double bonds.

The term "aromatic" refers an aromatic group or compound that typically has 3 to 40 carbon atoms or 3 to 30 carbon atoms. The aromatic group or compound can be carbocyclic, heterocyclic containing one or more of the heteroatoms (O, N, or S). The aromatic ring can have one ring or can have multiple fused rings that are each carbocyclic or heterocyclic.

The term "aryl" refers to a monovalent group that is aromatic and carbocyclic. The aryl has at least one aromatic ring. Optionally, the aromatic ring can have one or more additional carbocyclic rings that are fused to the aromatic ring. Any additional rings can be unsaturated, saturated, or aromatic. Unless otherwise indicated, the aryl groups typically contain from 6 to 30 carbon atoms. In some embodiments, the aryl groups contain 6 to 20, 6 to 18, 6 to 16, 6 to 12, or 6 to 10 carbon atoms. Examples of an aryl group include phenyl, naphthyl, biphenyl, phenanthryl, and anthracyl.

The term "arylene" refers to a divalent group that is aromatic and carbocyclic. The arylene has at least one aromatic ring. Optionally, the aromatic ring can have one or more additional carbocyclic rings that are fused to the aromatic ring. Any additional rings can be unsaturated, saturated, or aromatic. Unless otherwise specified, arylene groups often have 6 to 20 carbon atoms, 6 to 18 carbon atoms, 6 to 16 carbon atoms, 6 to 12 carbon atoms, or 6 to 10 carbon atoms.

The term "aralkyl" refers to a monovalent group that is an alkyl group substituted with an aryl group (e.g., as in a benzyl group); the aralkyl group can be considered as being an alkylene bonded to an aryl. Unless otherwise indicated, the alkyl (or alkylene) portion often has 1 to 10 carbon atoms, 1 to 6 carbon atoms, or 1 to 4 carbon atoms and the aryl portion often has 6 to 20 carbon atoms, 6 to 18 carbon atoms, 6 to 16 carbon atoms, 6 to 12 carbon atoms, or 6 to 10 carbon atoms.

The term "alkaryl" refers to a monovalent group that is an aryl substituted with an alkyl group (e.g., as in a tolyl group); the alkaryl can be considered as being an arylene bonded to an alkyl. Unless otherwise indicated, the alkyl portion often has 1 to 10 carbon atoms, 1 to 6 carbon atoms, or 1 to 4 carbon atoms and an aryl (or arylene) portion often has 6 to 20 carbon atoms, 6 to 18 carbon atoms, 6 to 16 carbon atoms, 6 to 12 carbon atoms, or 6 to 10 carbon atoms.

The term "hydrocarbyl" refers to a monovalent group that contains only hydrogen and carbon atoms and that can be saturated, partially unsaturated, or aromatic.

The term "hydrocarbylene" refers to a divalent group that contains only hydrogen and carbon atoms and that can be saturated, partially unsaturated, or aromatic.

The term "tissue" refers to mammalian tissue and includes skin and all deeper tissues.

The term "room temperature" refers to a temperature of 22° C. to 25° C.

The recitation of numerical ranges by endpoints includes the endpoints, all numbers within that range (e.g., 1 to 5 includes 1, 1.5, 2, 2.75, 3, 3.80, 4, and 5), and any range within that range.

DETAILED DESCRIPTION

A multiple-part curable composition is provided that can be combined and cured to form a cured composition. The multiple-part curable composition contains at least a part A and a part B. Part A contains an oxalamido-containing compound while part B contains a derivatized polyethylene imine. When combined, the oxalamido-containing compound and the derivatized polyethylene imine undergo a condensation reaction to form the cured composition.

The cured composition is typically an adhesive. When the adhesive is used as a tissue adhesive, both parts A and B are usually selected to be relatively hydrophobic. Hydrophobic components can be advantageous for preventing swelling in the presence of aqueous fluids such as blood or other bodily fluids. Further, if both parts A and B have similar hydrophobicity, they typically can be combined and mixed with greater ease to yield adhesives with properties desirable for use as an adhesive tissue.

Part A

The curable composition includes a part A comprising an oxalamido-containing compound having at least two oxalamido groups of formula —NR$^2$—(CO)—(CO)—OR$^1$, wherein R$^1$ is a hydrocarbyl and wherein R$^2$ is hydrogen or hydrocarbyl. Suitable hydrocarbyl groups for R$^1$ and R$^2$ typically have at least 1 carbon atom, at least 2 carbon atoms, at least 4 carbon atoms, at least 6 carbon atoms, or at least 7 carbon atoms and up to 12 carbon atoms or more, up to 10 carbon atoms, up to 8 carbon atoms, up to 6 carbon atoms, or up to 4 carbon atoms.

In many oxalamido groups, R$^1$ is an alkyl, aryl, aralkyl, or alkaryl and R$^2$ is hydrogen, alkyl, aryl, aralkyl, or alkaryl. Suitable alkyl groups often have 1 to 10 carbon atoms, 1 to 6 carbon atoms, or 1 to 4 carbon atoms. Suitable aryl groups typically have 6 to 10 carbon atoms and are often phenyl. Suitable aralkyl groups often have an aryl group with 6 to 10 carbon atoms (e.g., phenyl) and an alkylene group with 1 to 10 carbon atoms. The aralkyl is often benzyl. Suitable alkaryl groups often have an arylene group with 6 to 10 carbon atoms (e.g., phenylene) and an alkyl group with 1 to 10 carbon atoms. The alkaryl is often tolyl. In most embodiments, R$^2$ is hydrogen or alkyl and R$^1$ is an alkyl or aryl.

The oxalamido-containing compound has at least two oxalamido groups. The number of these groups can be, for example two, three, or four. In many embodiments, the oxalamido-containing compound has two oxalamido groups and is of Formula (II).

$$R^1O—(CO)—(CO)—[NR^2—R^4—NR^2—(CO)—(CO)]_q—OR^1 \quad (II)$$

In Formula (II), group $R^1$ is a hydrocarbyl, group $R^2$ is hydrogen or a hydrocarbyl, and group $R^4$ is a hydrocarbylene. The variable q is typically an integer in a range of 1 to 10.

The oxalamido-containing compound of Formula (II) can be prepared by the condensation reaction of an oxalate compound of Formula (I) with a diamine of Formula (III) as shown in Reaction Scheme A. Reaction Scheme A shows the reactants and products.

Reaction Scheme A

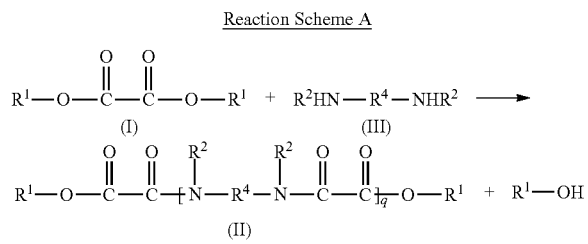

The oxalate of Formula (I) that is reacted with the diamine of Formula (III) can be prepared, for example, by reacting an alcohol of formula $R^1$—OH with oxalyl dichloride. Oxalates of Formula (I) are commercially available and include, but are not limited to, dimethyl oxalate, diethyl oxalate, di-n-butyl oxalate, di-tert-butyl oxalate, diisopropyl oxalate, dipropyl oxalate, dipentyl oxalate, tert-butyl ethyl oxalate, tert-butyl methyl oxalate, bis(4-methylbenzyl) oxalate, isobutyl octan-2-yl oxalate, dibenzyl oxalate, and bis(phenyl) oxalate.

The diamine of Formula (III) contains a hydrocarbylene $R^4$ group. This group is often selected to impart hydrophobic character, flexibility, and toughness to the oxalamido-containing compound. Group $R^4$ often has at least 6 carbon atoms, at least 8 carbon atoms, at least 10 carbon atoms, at least 12 carbon atoms, at least 16 carbon atoms, at least 18 carbon atoms, at least 20 carbon atoms, or at least 30 carbon atoms and up to 60 carbon atoms, up to 55 carbon atoms, up to 50 carbon atoms, up to 45 carbon atoms, up to 40 carbon atoms, or up to 36 carbon atoms. The hydrocarbylene can be saturated, partially unsaturated, or aromatic and can include groups that are linear, branched, cyclic, or a combination thereof. The hydrocarbylene is often selected from an alkylene, alkenene, arylene, or a combination thereof.

Some example diamines of Formula (III) have 5 to 30 carbon atoms. Examples include, but are not limited to, 2-methylpentane-1,5-diamine, 1,3-pentanediamine, 1,6-hexanediamine, 1,8-octanediamine, 1,10-decanediamine, 1,12-dodecanediamine, 4,4'-methylenebiscyclohexylamine, m-xylene diamine, p-xylene diamine, bis(aminomethyl)cyclohexane, isophorone diamine, octahydro-4,7-methano-1H-indenedimethylamine (available under the trade designation TCD DIAMINE from Oxea, Dallas, Tex), diaminocyclohexane, 4,4'-trimethylenedipiperidine, bis(aminoethyl)benzene, methylenedianiline, phenylenediamine, diaminonaphthalene, and toluenediamine.

In many embodiments, the compounds of Formula (III) have more than 30 carbon atoms. The compounds of Formula (III) with more carbon atoms often can impart greater hydrophobic character, increased flexibility, increased toughness, or a combination thereof to the final cured composition. Increased hydrophobicity can be desirable when the cured composition is a tissue adhesive because it is less likely to swell in the presence of body fluids. Example compounds of Formula (III) with more than 30 carbon atoms include dimer diamines, which usually contain 36 carbon atoms. Dimer diamines can be prepared from dimer acids, which are typically dicarboxylic acids. The dimer acids can be prepared by dimerizing unsaturated fatty acids such as those derived from tall oil. Dimer acids can be reacted with ammonia or an amine followed by reduction to prepare dimer diamines. Suitable dimer diamines are commercially available under the trade designation PRIAMINE from Croda Inc. (Edison, NJ, USA).

The equivalents ratio of the oxalate compound of Formula (I) to the diamine of Formula (III) can be used to control the value of the variable q in Formula (II) and the viscosity of part A. In some embodiments, the equivalents ratio of the oxalate compound to the diamine is at least 2, at least 4, at least 6, at least 8, or at least 10. Having a large excess of the oxalate compound relative to the diamine tends to favor the formation of an oxalamido-containing compound of Formula (II) with q being equal to 1.

The oxalamido-containing compounds of Formula (II) are often a mixture of compounds with different amounts of chain extension (i.e., different q values). In many embodiments, q is equal to one for most of the oxalamido-containing compounds in the mixture. In some embodiments, the variable q is equal to one for at least 70 weight percent, at least 80 weight percent, at least 80 weight percent, at least 90 weight percent, or at least 95 weight percent of the oxalamido-containing compounds in the mixture. The weight percent is based on a total weight of the mixture of oxalamido-containing compounds. Including some oxalamido-containing compounds with q being greater than 1 in the mixture can be used to adjust the viscosity (typically increase the viscosity) if needed to more closely match the viscosity of the part A with that of part B.

A mixture of different oxalamido-containing compounds of Formula (II) with different $R^4$ groups can be included in part A. For example, a first oxalamido-containing compound formed from a dimer diamine can be combined with a second oxalamido-containing compound formed from a diamine having 6 to 30 carbon atoms. This can be done, for example, to adjust the viscosity of part A (typically decrease the viscosity) to more closely match the viscosity of part B.

Any excess oxalate compound used to prepare the oxalamide-containing compound of Formula (II) is preferably removed prior to reaction of the oxalamido-containing compound of part A with the derivatized polyethylene imine of part B. For example, part A typically contains 0 to 5 weight percent of the oxalate compound of Formula (I) based on the total weight of reactive components in part A. In some embodiments, the amount of the oxalate compound in part A is no greater than 4 weight percent, no greater than 3 weight percent, no greater than 2 weight percent, no greater than 1 weight percent, no greater than 0.5 weight percent and at least 0.1 weight percent, at least 0.5 weight percent, or at least 1 weight percent based on the total weight of reactive components in part A. The term "reactive components" refers to those compounds that can react with the derivatized polyethylene imine in part B.

Further, the alcohol by-product ($R^1$—OH) of the condensation reaction used to form the oxalamido-containing compound is typically removed prior to reaction of the oxalamido-containing compound with the polyethylene derivative. The alcohol can be removed simultaneously with the excess oxalate compound using techniques well known in the art. For example, both compounds can be removed in a vacuum oven set at about 150 degrees Celsius.

In many embodiments, the amount of alcohol $R^1$—OH is present in an amount in a range of 0 to 5 weight percent based on a total weight of part A. If present, the amount of alcohol is often no greater than 4 weight percent, no greater than 3 weight percent, no greater than 2 weight percent, no greater than 1 weight percent, or no greater than 0.5 weight percent and at least 0.1 weight percent, at least 0.5 weight percent, or at least 1 weight percent.

If the viscosity of part A needs to be lowered to more closely match the viscosity of part B, an optional non-reactive organic solvent can be added to part A. Suitable non-reactive organic solvents are typically volatile at room temperature (e.g., 20 to 25 degrees Celsius) and atmospheric pressure. As used herein, "volatile" in reference to the non-reactive organic solvent means that it can evaporate rapidly at normal temperatures and pressure. For example, one metric drop (1/20 mL, 50 mu L) of a volatile solvent will evaporate completely under these conditions within 5 minutes, within 4 minutes, within 3 minutes, within 2 minutes, within 1 minute, within 30 seconds, or within 15 seconds.

Suitable optional non-reactive organic solvents include various volatile non-polar solvents, polar solvents, aprotic solvents, and mixtures thereof. Example volatile non-polar solvents include, but are not limited to, volatile linear, branched, and cyclic alkanes such as propane, isobutane, liquid butane (e.g., under pressure), pentane, hexane, heptane, octane, petroleum distillates, cyclohexane, and isooctane. Example volatile polar solvents include, but are not limited to, ethanol and isopropanol. Example volatile aprotic solvents include, but are not limited to, volatile acetates (e.g., methyl acetate, ethyl acetate, and propylene glycol diacetate), volatile ketones (e.g., acetone and methyl ethyl ketone), and volatile ethers (e.g., diethyl ether, ethyl propyl ether, dipropyl ether and dipropylene glycol dimethyl ether). Further, a volatile gas, such as carbon dioxide, can be used.

Part A can contain 0 to 5 weight percent of the optional non-reactive organic solvent based on a total weight of part A. For example, if present, the amount of the non-reactive organic solvents is often no greater than 4 weight percent, no greater than 3 weight percent, no greater than 2 weight percent, no greater than 1 weight percent, or no greater than 0.5 weight percent and at least 0.1 weight percent, at least 0.5 weight percent, or at least 1 weight percent. In some embodiments, part A is free or substantially free of the non-reactive organic solvents. As used in reference to the non-reactive organic solvents in part A, the term "substantially free" refers to part A compositions that contain less than 0.1 weight percent, less than 0.05 weight percent, or less than 0.01 weight percent of these compounds based on the total weight of part A.

Water may optionally be included in some part A compositions. The amount can be in a range of 0 to 5 weight percent based on the total weight of part A. For example, if present, the amount can be up to 5 weight percent, up to 4 weight percent, up to 3 weight percent, up to 2 weight percent, up to 1 weight percent, or up to 0.5 weight percent and at least 0.1 weight percent, at least 0.5 weight percent, or at least 1 weight percent. In some embodiments, part A is free or substantially free of water. As used in reference to water in part A, the term "substantially free" refers to part A compositions that contain less than 0.1 weight percent, less than 0.05 weight percent, or less than 0.01 weight percent water based on the total weight of part A.

Still further, Part A is typically free or substantially free of an oxalamido-containing compound with a siloxane segment. As used in reference to such compounds, the term "substantially free" means less than 0.1 weight percent, less than 0.05 weight percent, or less than 0.01 weight percent based on the total weight of oxalamido-containing compounds in part A.

In some embodiments, part A contains at least 85 weight percent of the oxalamido-containing compound based on the total weight of part A. For example, part A can contain at least 90 weight percent, at least 92 weight percent, at least 94 weight percent, at last 95 weight percent, at least 96 weight percent, at least 97 weight percent, at least 98 weight percent, or at least 99 weight percent and up to 100 weight percent of the oxalamido-containing compound based on the total weight of part A. The remainder of part A often includes one or more compounds selected from the oxalate compound, $R^1$—OH, the optional non-reactive organic solvent, water, or other optional components.

Part B

The curable composition includes a part B comprising a derivatized polyethylene imine (derivatized PEI). The derivatized polyethylene imine is a reaction product of a polyethylene imine with a glycidyl ether and contains monomeric units of Formula (VI) in addition to other types of monomeric units.

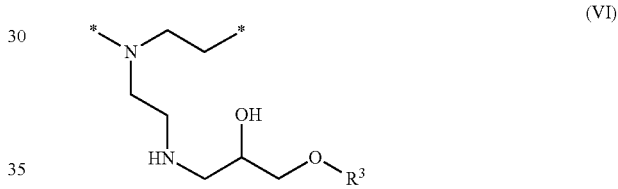

(VI)

In Formula (VI), the group $R^3$ is an alkyl having at least 4 carbon atoms, an aryl, an aralkyl, or an alkaryl and each asterisk (*) is an attachment site to another monomeric unit of the derivatized polyethylene imine Polyethylene imine (PEI) is commercially available in several forms such as linear, branched, and dendrimeric polymers. Linear PEIs contain mainly secondary amino groups with primary amino groups at the polymeric chain ends. Branched PEIs typically have more primary amino groups than linear PEIs. Branched PEI can be synthesized by the ring opening polymerization of aziridine. Branched PEIs are commercially available or can be made according to known methods. The extent of branching within the PEI determines the relative molar ratios of primary amino groups: secondary amino groups: tertiary amino groups. The branched PEIs often contain about 25 to about 50 mole percent primary amino groups, about 25 to about 50 mole percent secondary amino groups, and about 25 to about 50 mole percent tertiary amino groups based on the total moles of amino groups in the PEI. Dendrimeric PEIs usually contain only primary and tertiary amino groups. Dendrimeric PEIs are commercially available and/or can be made according to known methods. Branched PEIs are often used to form the derivatized PEI by reaction with the glycidyl ether.

The derivatized PEI can be formed from a branched polyethylene imine having monomeric units of Formula (IV) and (V) wherein each asterisk (*) is as defined above.

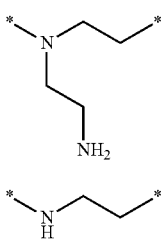

(IV)

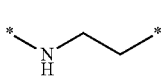

(V)

The polyethylene imine is reacted with a glycidyl ether of Formula (VIII)

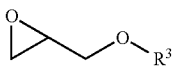

(VIII)

wherein $R^3$ is an alkyl having at least 4 carbon atoms, aryl, aralkyl, or alkaryl. Alkyl $R^3$ groups usually have at least 4 carbon atoms, at least 6 carbon atoms, at least 8 carbon atoms, or at least 10 carbon atoms and up to 30 carbon atoms, up to 24 carbon atoms, up to 20 carbon atoms, up to 18 carbon atoms, up to 16 carbon atoms, up to 12 carbon atoms, up to 10 carbon atoms, or up to 8 carbon atoms. Any suitable aryl, aralkyl, or alkaryl group can be used but the aryl group is often phenyl (i.e., the glycidyl ether is phenyl glycidyl ether), the aralkyl group is often benzyl (i.e., the glycidyl ether is benzyl glycidyl ether), and the alkaryl group is often tolyl (i.e, the glycidyl ether is tolyl glycidyl ether). Reaction with the glycidyl ether tends to increase the hydrophobicity of the derivatized PEI compared to the PEI prior to derivatization.

In many embodiments, the glycidyl ether of Formula (VIII) is an alkyl glycidyl ether such as n-butyl glycidyl ether, heptyl glycidyl ether, 2-ethylhexyl glycidyl ether, octyl glycidyl ether, decyl glycidyl ether, dodecyl glycidyl ether, tetradecyl glycidyl ether, or a mixture thereof. The hydrophobicity often can be increased by selection of a longer alkyl group $R^3$ in the alkyl glycidyl ether.

The glycidyl ether of Formula (VIII) can react with both the polyethylene imine monomeric units of Formula (IV) having a primary amino group and of Formula (V) having a secondary amino group. The reaction results in the ring opening of the epoxy group in Formula (VIII) and the covalent attachment of the glycidyl ether to form the derivatized PEI having monomeric units of Formulas (VI) and or both Formulas (VI) and (VII).

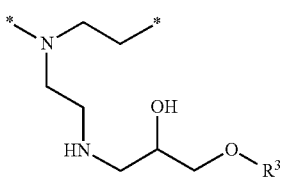

(VI)

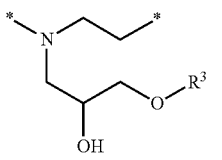

(VII)

Formula (VI) results from a reaction of the glycidyl ether of Formula (VIII) with a primary amino group in the monomeric units of Formula (IV) in the PEI while Formula (VII) results from a reaction of the glycidyl ether with a secondary amino group in the monomeric unit of Formula (V) in the PEI. The glycidyl ether can usually react more easily with primary amino groups.

Typically, enough glycidyl ether is reacted with the monomeric units of Formula (IV) and/or Formula (V) to provide 10 to 25 mole percent Formula (VI) and/or Formula (VII) in the derivatized PEI. The amount is based on total moles of monomeric units in the derivatized PEI. For example, at least 10 mole percent, at least 12 mole percent, or at least 15 mole percent and up to 25 mole percent, up to 22 mole percent, up to 20 mole percent, up to 18 mole percent, or up to 15 mole percent of the total monomeric units in the derivatized PEI are of Formula (VI) and/or Formula (VII). If less than 10 mole percent of the monomeric units are of Formula (VI) and/or Formula (VII), the derivatized PEI may not be sufficiently hydrophobic. Preferably, some primary amino groups remain unreacted for later reaction with oxalamido-containing compound in part A. That is, preferably the derivatized PEI contains monomeric units of Formula (IV).

The derivatized PEI can contain monomeric units of Formula (IV), Formula (V), Formula (VI) and Formula (VII). Because the primary amino groups of the monomeric units of Formula (IV) tend to react more readily than the secondary amino groups of Formula (V) with the glycidyl ether, the derivatized PEI usually contains more monomeric units of Formula (VI) than of Formula (VII).

Suitable polyethylene imines are typically selected to be a liquid at room temperature and preferably are not dissolved in water. The polyethylene imine, prior to being subjected to derivatization, often has a number average molecular weight in a range of 600 to 25,000 Daltons (Da). For example, the number average molecular weight can be at least 600 Da, at least 800 Da, at least 1000 Da, at least 1200 Da, at least 1500 Da, at least 2000 Da, at least 4000 Da, at least 5000 Da, or at least 10,000 Da and up to 25,000 Da, up to 20,000 Da, up to 15,000 Da, up to 12,000 Da, up to 10,000 Da. The number average molecular weight can be measured, for example, using gel permeation chromatography with polystyrene standards.

The molecular weight of the polyethylene imine is often selected so that the viscosity of part B is relatively close to the viscosity of part A. The viscosity of part B can be adjusted in various ways. For example, a mixture of different derivatized PEI can be included in part B. The mixture can include, for example, a mixture of a first derivatized PEI and a second derivatized PEI, wherein the PEI used to form the first derivatized PEI has a lower molecular weight than the PEI used to form the second derivatized PEI. The relative amounts of the first derivatized PEI and the second derivatized PEI can be varied to adjust the viscosity of part B.

If the viscosity of part B is too high, it also can be reduced by the addition of an optional second amino-containing compound having at least two primary and/or secondary amino group and having a lower viscosity than the derivatized PEI. Suitable optional second amine compounds that can be included in part B include various amine compounds having 2 to 16 carbon atoms such as ethylene diamine, 1,2-propanediamine, 1,3-propanediamine, 1,4-butanediamine, 2-methylpentane-1,5-diamine, 1,6-hexanediamine, 1,8-octanediamine, 1,10-decanediamine, 1,12-dodecanediamine, 4,4'-methylenebiscyclohexylamine, m-xylene diamine, p-xylene diamine, bis(aminomethyl)cyclohexane, piperazine, isophorone diamine, N-(2-aminoethyl)piperazine, N,N'-bis(3-aminopropyl)piperazine, tris(2-aminoethyl)amine, 3,3'-diaminodipropylether, 1,13-diamino-4,7,10-trioxatridecane, octahydro-4,7-methano-1H-indenedimethylamine (available under the trade designation TCD DIAMINE from Oxea, Dallas, TX).

If desired, part B can include optional second amino-containing compounds having more than two amino groups to increase the crosslinking of the cured composition. Such compounds include, for example, tris(2-aminoethyl)amine, diethylenetriamine, triethylenetetramine, and the like.

Various polymeric materials can also be used as the optional second amino-containing compound. The molecular weights of these optional polymers are often lower than that of the derivatized PEI. Suitable optional second amino-containing compounds that are polymers include, for example, polyaminoamides, polyvinylamines, polyallylamines, and polydiallylamines.

Part B often contains 0 to 10 weight percent of the optional second amino-containing compound based on the total weight of part B. For example, the amount can be up to 10 weight percent, up to 8 weight percent, up to 6 weight percent, up to 5 weight percent, up to 4 weight percent, up to 3 weight percent, up to 2 weight percent, up to 1 weight percent, or up to 0.5 weight percent and at least 0.1 weight percent, at last 0.5 weight percent, or at least 1 weight percent. If a hydrophilic second amine (e.g., such as one having an ether or polyether group) is used, it is often used in a small amount (e.g., up to 5 weight percent, up to 3 weight percent, or up to 1 weight percent) so that the overall part B composition remains sufficiently hydrophobic. In some embodiments, part B is free or substantially free of the second amino-containing compound. As used in reference to the second amino-containing compound in part B, the term "substantially free" refers to part B compositions that contain less than 0.1 weight percent, less than 0.05 weight percent, or less than 0.01 weight percent water based on the total weight of part B.

The viscosity of part B can also be reduced by the addition of an optional non-reactive organic solvent. The same optional non-reactive organic solvents discussed above for use in part A can be used in part B. Part B can contain 0 to 5 weight percent of the optional non-reactive organic solvent based on a total weight of part B. For example, the amount of the non-reactive organic solvents, if present, is often no greater than 4 weight percent, no greater than 3 weight percent, no greater than 2 weight percent, no greater than 1 weight percent, or no greater than 0.5 weight percent and at least 0.1 weight percent, at least 0.5 weight percent, or at least 1 weight percent. In some embodiments, part B is free or substantially free of the non-reactive organic solvents. As used in reference the non-reactive organic solvents in part B, the term "substantially free" refers to compositions that contain less than 0.1 weight percent, less than 0.05 weight percent, or less than 0.01 weight percent of these compounds based on the total weight of part B.

Water may optionally be included in some part B compositions. The water can be present, for example, in the PEI that is derivatized with the glycidyl ether. The amount of water in part B can be in a range of 0 to 5 weight percent based on the total weight of part B. For example, if present, the amount can be up to 4 weight percent, up to 3 weight percent, up to 2 weight percent, up to 1 weight percent, up to 0.5 weight percent, or up to 0.1 weight percent. In some embodiment, part B is free or substantially free of water. As used in reference water in part B, the term "substantially free" refers to part B compositions that contain less than 0.1 weight percent, less than 0.05 weight percent, or less than 0 01 weight percent water based on the total weight of part B.

The viscosity of part B is preferably somewhat close to the viscosity of part A. If the two viscosities are somewhat close, the two parts can be more easily combined using a dual syringe connected to a mixing chamber and then delivered to a location of interest. If part A has a first viscosity (V1) and part B has a second viscosity (V2), the second viscosity (V2) is often a range of 0.1(V1) to 10(V1). The viscosity V2 can be at least 0.1(V1), at least 0.2(V1), at least 0.5(V1), at least 1(V1), at least 2(V1) and up to 10(V1), up to 5(V1), up to 3(V1), up to 2(V1), up to 1(V1), or up to 0.5(V1). Viscosity can be measured, for example, using the method described in the Example section. The viscosity of each part A and part B is often in a range of 5 to 50 Pascals-second.

In some embodiments, part B contains at least 90 weight percent of the derivatized PEI based on the total weight of part B. For example, part B can contain at least 92 weight percent, at least 94 weight percent, at last 95 weight percent, at least 96 weight percent, at least 97 weight percent, at least 98 weight percent, or at least 99 weight percent of the derivatized PEI based on the total weight of part B. The remainder of part B often includes one or more compounds selected from the second amino-compound, optional non-reactive organic solvent, water, or other optional components.

Additional Optional Components

Optional components can be included in part A, part B, or even in an additional part C. Optional components added to part A are typically selected so that they do not react with the oxalamido-containing compound. Similarly, optional components added to part B are typically selected so that they do not react with the derivatized PEI.

For use of the cured composition as a tissue adhesive, part A and/or part B can include optional components such as surfactants (e.g., non-ionic surfactants), antimicrobial agents, antioxidants, adhesion promoters, fillers, dyes, and the like. The non-ionic surfactants can be used to adjust the viscosity of part A and/or part B and/or improve the compatibility of part A with part B.

In some embodiments, a fatty acid is added to Part A and/or Part B. If added to Part A, the carboxylic acid can increase the adhesive strength of the cured composition to skin depending on the carboxylic acid selected and the amount of the carboxylic acid. While not wishing to be bound by theory, the carboxylic acid may migrate to the tissue surface and promote adhesion of the curable and/or cured compositions to the tissue surface. Better adhesion to the tissue surface may lead to enhanced adhesive strength.

The carboxylic acid often has 4 to 24 carbon atoms and can be saturated or unsaturated. The carboxylic acid can have, for example, at least 4, at least 6, at least 8, at least 10, or at least 12 carbon atoms and up to 24, up to 20, up to 18, up to 16, up to 14, or up to 12 carbon atoms. Carboxylic acids with a higher molecular weight often tend to increase the adhesive strength more than those with a lower molecular weight. In some embodiments, the carboxylic acid is a fatty acid.

Examples of suitable carboxylic acids include, but are not limited to, hexanoic acid, octanoic acid, decanoic acid, dodecanoic acid, tetradecanoic acid, hexadecenoic acid, eicosanoic acid, stearic acid, isostearic acid, oleic acid, linoleic acid, and erucic acid.

The amount of the carboxylic acid used effects the adhesive strength. The amount is often 0.01 to 10 weight percent based on the total weight of part (i.e., part A or part B) to which it is added. For example, the amount can be at least 0.01 weight percent, at least 0.05 weight percent, at least 0.1 weight percent, at least 0.2 weight percent, at least 0.3 weight percent, at least 0.5 weight percent, at least 1 weight percent, or at least 2 weight percent and up to 10 weight percent, up to 8 weight percent, up to 6 weight percent, up to 5 weight percent, up to 4 weight percent, up to 3 weight percent, up to 2 weight percent, or up to 1 weight percent. The preferred amount can vary with the molecular weight of the carboxylic acid.

Cured Composition

The cured composition is formed by combining the multiple parts of the curable composition. That is, part A and part B plus any optional additional parts are combined. This combination results in a condensation reaction between the at least two oxalamido groups of the oxalamido-containing compound in part A and the primary and secondary amino groups of the derivatized PEI in part B. In many embodiments, the oxalamido-containing compound reacts preferentially with the primary amino groups (i.e., monomeric units of Formula (IV)) of the derivatized PEI. The cured composition is crosslinked and is usually an adhesive.

The cured composition is typically formed by preparing or obtaining the part A composition as described above, preparing or obtaining the part B composition as described above, combining part A with part B to form a reaction mixture, and positioning the reaction mixture on a surface to form the cured composition. Part A and part B can be reacted to form the cured composition under any conditions suitable for the condensation reaction between the oxalamido-containing compound in part A and the derivatized PEI in part B. In some embodiments, part A and part B are combined at room temperature and/or cured at the temperature of a human body (e.g. about 37° C.). Higher temperatures can be used, if desired. For example, the reaction temperature can be from room temperature up to 100° C., up to 80° C., up to 60° C., up to 50° C., or up to 40° C. Part A and part B can be combined under ambient conditions without the need for a nitrogen purge.

In some embodiments, part A and part B are combined using mixing and/or dispensing methods and/or devices known in the art, such as by manual mixing or by using a mechanical mixing device, an automatic mixing device, a static mixing device, an extrusion mixing device, or a combination thereof. For example, part A can be present in a first chamber of a multi-chambered mixing and/or dispensing device (e.g., a first barrel of a dual barreled syringe), and part B can be present in a second chamber of a multi-chambered mixing and/or dispensing device (e.g., a second barrel of a dual barreled syringe).

Thus, in another aspect, a multi-chambered mixing and/or dispensing device is provided that contains the multi-part curable composition described above. Part A is present in a first chamber of the multi-chambered mixing and/or dispensing device, and part B is present in a second chamber of the multi-chambered mixing and/or dispensing device. In certain embodiments, the multi-chambered mixing and/or dispensing device is a dual barreled syringe containing the multi-part curable composition with part A in a first barrel of the dual barreled syringe and part B in a second barrel of the dual barreled syringe. Optionally, the dual barreled syringe may include or be connected to a static mixing device to mix the contents of each barrel upon delivery from the syringe and prior to discharging the reaction mixture (i.e., mixed composition) on the location of interest. While some curing may occur within the mixing device, the reaction mixture is typically still fluid when discharged from the mixing device.

Although not required, the volume of part A is often selected to be the same or nearly the same as the volume of part B. The content of the two syringes are combined before the reaction mixture is positioned at the location of interest.

Because the oxalamido-containing compound reacts most easily with the primary amino groups in the derivatized PEI, the amount of derivatized PEI is based on the moles of primary amino groups in the derivatized PEI. The molar ratio of primary amino groups of the derivatized PEI in part B to oxalamido-containing compound of Formula (I) in part A (i.e., moles of primary amino groups in the derivatized PEI to moles of oxalamido-containing compound) is in a range of 0.75 to 3.5. The molar ratio is at least 0.75, at least 0.8, at least 0.9, at least 1.0, at least 1.2, at least 1.4, at least 1.5, at last 1.6, at least 1.8, at least 2.0, at least 2.2, or at least 2.5 and up to 3.5, up to 3.4, up to 3.2, up to 3.0, up to 2.8, up to 2.6, up to 2.5, up to 2.4, up to 2.2, up to 2.0, up to 1.8, up to 1.6, or up to 1.5.

The cured composition can be used as a tissue adhesive. Stated differently, the mixed composition of part A and part B can be discharged onto the surface of mammalian tissue for curing. The tissue adhesive can be a topical tissue adhesive such as a skin adhesive or can be used for closing wounds. For example, the tissue adhesive can replace sutures and staples in closing wounds. The reaction mixture used to form the cured composition has a viscosity that is suitably high so that it can be accurately positioned at the desired location on the tissue and so that it will not spread undesirably to other surfaces.

For use as a tissue adhesive, the cured composition desirably has a percent elongation at break that is in a range of 20 to 80 percent using ASTM method D882-2018. If the elongation at break is less than 20 percent, the cured composition may not be sufficiently flexible. If the elongation at break is greater than 80 percent, however, the cured composition may not effectively close a wound. The percent elongation at break can be at least 20 percent, at least 30 percent, at least 40 percent, or at least 50 percent and up to 80 percent, up to 60 percent, or up to 50 percent.

For use as a tissue adhesive, the cured composition desirably has a wound closure strength of at least 2 Newtons, at least 2.5 Newtons, at least 3 Newtons, at least 3.5 Newtons, at least 4 Newtons, at least 4.5 Newtons, at least 5 Newtons, at least 5.5 Newtons, at least 6 Newtons, at least 6.5 Newtons, or at least 7 Newtons using ASTM method F2458-05. If the closure strength is less than 5 Newtons, the wound closure may be opened too easily.

When part A reacts with part B, the condensation reaction occurs in a relatively short period of time and usually results in a relatively low exotherm. That is, the reaction typically does not generate excessive heat and is well suited for used for use on skin or human tissue. For example, the exotherm typically does not exceed 40° C. and the reaction time for curing is often less than 120 seconds, less than 90 seconds, less than 60 seconds, or less than 45 seconds.

In addition to use as a tissue adhesive, the cured compositions can be used for adhering a wide range of materials to each other. For example, the cured compositions can be used to join a variety of polymeric materials to other polymeric materials or to glass, ceramic materials, metallic materials, and the like.

EXAMPLES

TABLE 1

Materials List

| Description (Abbreviation) | Source |
| --- | --- |
| Polyethylene imine (PEI 1200), Molecular Weight 1200 g/mol | Polysciences, Warrington, PA |
| Polyethylene imine (PEI 1200), Molecular Weight 1200 g/mol (trade designation: LOXANOL MI 6721) | BASF Corporation, Charlotte, NC |
| Polyethylene imine (PEI 600), Molecular Weight 600 g/mol | Polysciences, Warrington, PA |
| n-Butyl glycidyl ether (CAS No. 2426-08-6; Product No. 291455) | Sigma-Aldrich Company, St. Louis, MO |
| 2-Ethylhexyl glycidyl ether (CAS No. 2461-15-6; Product No. 251747) | Sigma-Aldrich Company, St. Louis, MO |
| Octyl/decyl glycidyl ether (CAS No. 68609-96-1; Product No. 412821) | Sigma-Aldrich Company, St. Louis, MO |
| Dodecyl/tetradecyl glycidyl ethers (CAS No. 68609-97-2; Product No. 412848) | Sigma-Aldrich Company, St. Louis, MO |
| Glycidyl hexadecyl ether (CAS No. 15965-99-8; Product No. 473642) | Sigma-Aldrich Company, St. Louis, MO |
| Diethyl oxalate (DEO) | Alfa Acsar Company, Haverhill, MA |
| PRIAMINE 1075 - C36 dimer diamine | Croda International, Edison, NJ |
| 2-Methylpentane-1,5-diamine | TCI America, Portland, OR |
| Hexanoic acid | Alfa Aesar Company, Haverhill, MA |
| Octanoic acid | Alfa Acsar Company, Haverhill, MA |
| Decanoic acid | Alfa Aesar Company, Haverhill, MA |
| Isostearic acid (CAS No. 54680-48-7) | TCI America, Portland, OR |
| 2-Heptylundecanoic acid (CAS No. 22890-21-7) | TCI America, Portland, OR |
| Oleic acid | Alfa Acsar Company, Haverhill, MA |
| 1-Octanol | Alfa Aesar Company, Haverhill, MA |
| 1,2-Octanediol | Alfa Aesar Company, Haverhill, MA |

Preparatory Examples for Part A of Curable Compositions

Preparatory Example 1: Bis-oxamic acid ethyl ester of PRIAMINE 1075

Diethyl oxalate (54.5 g, 373 mmol) was added to a 250 mL, 3-neck flask and stirred at ambient temperature using a mechanical stirrer (stirrer setting at about 700 rpm). PRIAMINE 1075 (50.0 g, 93.3 mmol) was added to the flask dropwise over a period of two hours using a syringe pump. Following the addition of PRIAMINE 1075, the mixture was stirred for an additional two hours at ambient temperature. The light-yellow liquid was transferred to an aluminum pan. The pan was placed in a vacuum oven (set at 50 mm Hg, 150° C.) for eight hours to remove ethanol byproduct and unreacted diethyl oxalate. The resulting bis-oxamic acid ethyl ester of PRIAMINE 1075 was obtained as a light-yellow, viscous oil.

Preparatory Example 2: 2-Methylpentylene-bis-oxamic acid ethyl ester

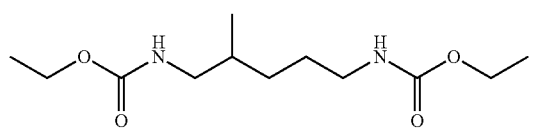

Diethyl oxalate (252 g, 1720 mmol) was added to a 500-mL, 3-neck flask and vigorously stirred at ambient temperature using a mechanical stirrer. 2-Methylpentane-1,5-diamine (50.0 g, 430 mmol) was added to the flask dropwise over a period of two hours using a syringe pump. Following the addition of 2-methylpentane-1,5-diamine, the light-yellow mixture was stirred for an additional two hours at ambient temperature. The reaction mixture was transferred to an aluminum pan and concentrated in a vacuum oven (set at 50 mmHg, 150° C.) for eight hours to remove ethanol byproduct and unreacted diethyl oxalate. The resulting 2-methylpentylene-bis-oxamic acid ethyl ester was obtained as a light yellow, viscous liquid.

Preparatory Example 3: DEO (5 Weight %) Added to Preparatory Example 1

The bis-oxamic acid ethyl ester of PRIAMINE 1075 prepared in Preparatory Example 1 (19 g) and diethyl oxalate (1.0 g) were added to a 50 mL screw cap vial. The vial was capped and the contents were mixed at ambient temperature for two hours using a bottle roller to give a homogeneous liquid.

Preparatory Example 4: Hexanoic acid (10 Weight %) Added to Preparatory Example 1

The bis-oxamic acid ethyl ester of PRIAMINE 1075 prepared in Preparatory Example 1 (18.0 g) and hexanoic acid (2.0 g) were added to a 30 mL screw cap vial. The vial was capped and the contents were mixed at ambient temperature overnight using a bottle roller to give a homogeneous liquid.

Preparatory Example 5: Octanoic acid (5 Weight %) Added to Preparatory Example 1

The bis-oxamic acid ethyl ester of PRIAMINE 1075 prepared in Preparatory Example 1 (19.0 g) and octanoic acid (1.0 g) were added to a 30 mL screw cap vial. The vial was capped and the contents were mixed at ambient temperature overnight using a bottle roller to give a homogeneous liquid.

Preparatory Example 6: Octanoic acid (2.5 Weight %) Added to Preparatory Example 1

The bis-oxamic acid ethyl ester of PRIAMINE 1075 prepared in Preparatory Example 1 (19.5 g) and octanoic acid (0.5 g) were added to a 30 mL screw cap vial. The vial was capped and the contents were mixed at ambient temperature overnight using a bottle roller to give a homogeneous liquid.

Preparatory Example 7: Octanoic acid (1 Weight %) Added to Preparatory Example 1

The bis-oxamic acid ethyl ester of PRIAMINE 1075 prepared in Preparatory Example 1 (14.85 g) and octanoic acid (0.15 g) were added to a 30 mL screw cap vial. The vial was capped and the contents were mixed at ambient temperature overnight using a bottle roller to give a homogeneous liquid.

Preparatory Example 8: 1-Octanol (2.5 Weight %) Added to Preparatory Example 1

The bis-oxamic acid ethyl ester of PRIAMINE 1075 prepared in Preparatory Example 1 (14.62 g) and 1-octanol (0.38 g) were added to a 30 mL screw cap vial. The vial was capped and the contents were mixed at ambient temperature overnight using a bottle roller to give a homogeneous liquid.

Preparatory Example 9: 1,2-Octanediol (2.5 Weight %) Added to Preparatory Example 1

The bis-oxamic acid ethyl ester of PRIAMINE 1075 prepared in Preparatory Example 1 (14.62 g) and 1,2-octanediol (0.38 g) were added to a 30 mL screw cap vial. The vial was capped and the contents were mixed at ambient temperature overnight using a bottle roller to give a homogeneous liquid.

Preparatory Example 10: Decanoic acid (2.5 Weight %) Added to Preparatory Example 1

The bis-oxamic acid ethyl ester of PRIAMINE 1075 prepared in Preparatory Example 1 (14.62 g) and decanoic acid (0.38 g) were added to a 30 mL screw cap vial. The vial was capped and the contents were mixed at ambient temperature overnight using a bottle roller to give a homogeneous liquid.

Preparatory Example 11: Decanoic acid (1 Weight %) Added to Preparatory Example 1

The bis-oxamic acid ethyl ester of PRIAMINE 1075 prepared in Preparatory Example 1 (14.85 g) and decanoic acid (0.15 g) were added to a 30 mL screw cap vial. The vial was capped and the contents were mixed at ambient temperature overnight using a bottle roller to give a homogeneous liquid.

Preparatory Example 12: 2-Heptylundecanoic acid (2.5 Weight %) Added to Preparatory Example 1

The bis-oxamic acid ethyl ester of PRIAMINE 1075 prepared in Preparatory Example 1 (19.5 g) and 2-heptylundecanoic acid (0.5 g) were added to a 30 mL screw cap vial. The vial was capped and the contents were mixed at ambient temperature overnight using a bottle roller to give a homogeneous liquid.

Preparatory Example 13: 2-Heptylundecanoic acid (1 Weight %) Added to Preparatory Example 1

The bis-oxamic acid ethyl ester of PRIAMINE 1075 prepared in Preparatory Example 1 (19.8 g) and 2-heptylundecanoic acid (0.2 g) were added to a 30 mL screw cap vial. The vial was capped and the contents were mixed at ambient temperature overnight using a bottle roller to give a homogeneous liquid.

Preparatory Example 14: Isostearic acid (2.5 Weight %) Added to Preparatory Example 1

The bis-oxamic acid ethyl ester of PRIAMINE 1075 prepared in Preparatory Example 1 (19.5 g) and isostearic acid (0.5 g) were added to a 30 mL screw cap vial. The vial was capped and the contents were mixed at ambient temperature overnight using a bottle roller to give a homogeneous liquid.

Preparatory Example 15: Isostearic acid (1 Weight %) Added to Preparatory Example 1

The bis-oxamic acid ethyl ester of PRIAMINE 1075 prepared in Preparatory Example 1 (19.8 g) and isostearic acid (0.2 g) were added to a 30 mL screw cap vial. The vial was capped and the contents were mixed at ambient temperature overnight using a bottle roller to give a homogeneous liquid.

Preparatory Example 16: Oleic acid (2.5 Weight %) Added to Preparatory Example 1

The bis-oxamic acid ethyl ester of PRIAMINE 1075 prepared in Preparatory Example 1 (19.5 g) and oleic acid (0.5 g) were added to a 30 mL screw cap vial. The vial was capped and the contents were mixed at ambient temperature overnight using a bottle roller to give a homogeneous liquid.

Preparatory Example 17: Oleic acid (1 Weight %) Added to Preparatory Example 1

The bis-oxamic acid ethyl ester of PRIAMINE 1075 prepared in Preparatory Example 1 (19.8 g) and oleic acid (0.2 g) were added to a 30 mL screw cap vial. The vial was capped and the contents were mixed at ambient temperature overnight using a bottle roller to give a homogeneous liquid.

Preparatory Examples for Part B of Curable Compositions

Part B compounds were prepared based on the total molar amine content (sum of primary, secondary, and tertiary amines per mole of PEI) of the PEI compounds. The total molar amine content values for PEI 600 and PEI 1200 are shown in Table 2. The total molar amine content value for each molecular weight was obtained by dividing the average PEI molecular weight (MW) by the PEI repeat unit molecular weight of 43.04 g/mol (—$C_2H_5N$—). The amine content (primary, secondary, and tertiary) of each PEI was determined using the $^{13}$C-NMR procedure described by Holycross and Chai in *Macromolecules*, 2013, 46, pages 6891-6897. Each PEI sample was dissolved in D$_2$O and NMR spectra were acquired using a Bruker AVANCE 600 MHz NMR spectrometer (Bruker Corporation, Billerica, MA) equipped with an inverse cryoprobe. A $^{13}$C T1 experiment was conducted to determine all resonances that had T1 values 0.7 seconds or less. A recycle delay of 7 seconds was used for quantitative determinations. The results are reported in Table 2.

TABLE 2

Amine Content of PEIs

| Compound | Average PEI MW (g/mol) | Total Molar Amine Content | % Primary Amine Content | % Secondary Amine Content | % Tertiary Amine Content |
|---|---|---|---|---|---|
| PEI 600 | 600 | 14 | 38.5% | 37.8% | 23.7% |
| PEI 1200 | 1200 | 28 | 36.0% | 36.2% | 27.8% |

Preparatory Example 18: n-Butyl glycidyl ether-Modified PEI 1200 (10 Mol % of amines in PEI Modified)

PEI 1200 (LOXANOL MI 6721, 50 g, 1166.6 mmol of total amine content in PEI 1200) and n-butyl glycidyl ether (15.1 g, 116 mmol) were added to a 4 ounce jar. The jar was capped and rolled at ambient temperature for 28 hours to give n-butyl glycidyl ether-modified PEI as a colorless, viscous liquid. Based on the stoichiometry of the reactants, 10 mol % of the total amine content in PEI 1200 was modified by reacting with n-butyl glycidyl ether.

Preparatory Example 19: n-Butyl glycidyl ether-Modified PEI 1200 (15 Mol % of amines in PEI Modified)

PEI 1200 (LOXANOL MI 6721, 50 g, 1166.6 mmol of total amine content in PEI 1200) and n-butyl glycidyl ether (22.8 g, 175 mmol) were added to a 4 ounce jar. The jar was capped and rolled at ambient temperature for 28 hours to give n-butyl glycidyl ether-modified PEI as a colorless, viscous liquid. Based on the stoichiometry of the reactants, 15 mol % of the total amine content in PEI 1200 was modified by reacting with n-butyl glycidyl ether.

Preparatory Example 20: Octyl/decyl glycidyl ether-Modified PEI 1200 (10 Mol % of amines in PEI Modified)

PEI 1200 (15 g, 350 mmol of total amine content in PEI 1200) and octyl/decyl glycidyl ether (7.1 g, 35 mmol) were added to a 250 mL round bottom flask. The mixture was stirred at 40° C. for 12 hours to give octyl/decyl glycidyl ether-modified PEI as a colorless, viscous liquid. Based on the stoichiometry of the reactants, 10 mol % of the total amine content in PEI 1200 was modified by reacting with octyl/decyl glycidyl ether.

Preparatory Example 21: Octyl/decyl glycidyl ether-Modified PEI 1200 (15 Mol % of amines in PEI Modified)

PEI 1200 (15 g, 350 mmol of total amine content in PEI 1200) and octyl/decyl glycidyl ether (10.5 g, 52.5 mmol) were added to a 250 mL round bottom flask. The mixture was stirred at 40° C. for 12 hours to give octyl/decyl glycidyl ether-modified PEI as a colorless, viscous liquid. Based on the stoichiometry of the reactants, 15 mol % of the total amine content in PEI 1200 was modified by reacting with octyl/decyl glycidyl ether.

Preparatory Example 22: Octyl/decyl glycidyl ether-Modified PEI 1200 (20 Mol % of amines in PEI Modified)

PEI 1200 (15 g, 350 mmol of total amine content in PEI 1200) and octyl/decyl glycidyl ether (14.0 g, 70 mmol) were added to a 250 mL round bottom flask. The mixture was stirred at 40° C. for 12 hours to give octyl/decyl glycidyl ether-modified PEI as a colorless, viscous liquid. Based on the stoichiometry of the reactants, 20 mol % of the total amine content in PEI 1200 was modified by reacting with octyl/decyl glycidyl ether.

Preparatory Example 23: Octyl/decyl glycidyl ether-Modified PEI 600 (10 Mol % of amines in PEI Modified)

PEI 600 (15 g, 350 mmol of total amine content in PEI 600) and octyl/decyl glycidyl ether (7.1 g, 35 mmol) were added to a 250 mL round bottom flask. The mixture was stirred at 40° C. for 12 hours to give octyl/decyl glycidyl ether-modified PEI as a colorless, viscous liquid. Based on the stoichiometry of the reactants, 10 mol % of the total amine content in PEI 600 was modified by reacting with octyl/decyl glycidyl ether.

Preparatory Example 24: Octyl/decyl glycidyl ether-Modified PEI 600 (15 Mol % of amines in PEI Modified)

PEI 600 (15 g, 350 mmol of total amine content in PEI 600) and octyl/decyl glycidyl ether (10.5 g, 52.5 mmol) were added to a 250 mL round bottom flask. The mixture was stirred at 40° C. for 12 hours to give octyl/decyl glycidyl ether-modified PEI as a colorless, viscous liquid. Based on the stoichiometry of the reactants, 15 mol % of the total amine content in PEI 600 was modified by reacting with octyl/decyl glycidyl ether.

Preparatory Example 25: Octyl/decyl glycidyl ether-Modified PEI 600 (20 Mol % of amines in PEI Modified)

PEI 600 (15 g, 350 mmol of total amine content in PEI 600) and octyl/decyl glycidyl ether (14.0 g, 70 mmol) were added to a 250 mL round bottom flask. The mixture was stirred at 40° C. for 12 hours to give octyl/decyl glycidyl ether-modified PEI as a colorless, viscous liquid. Based on the stoichiometry of the reactants, 20 mol % of the total amine content in PEI 600 was modified by reacting with octyl/decyl glycidyl ether.

Preparatory Example 26: 2-Ethylhexyl glycidyl ether-Modified PEI 1200 (10 Mol % of amines in PEI Modified)

PEI 1200 (LOXANOL MI 6721, 45 g, 1050 mmol of total amine content in PEI 1200) and 2-ethylhexyl glycidyl ether (19.5 g, 104 mmol) were added to a 4 ounce jar. The jar was capped and rolled at ambient temperature for 28 hours to give 2-ethylhexyl glycidyl ether-modified PEI as a colorless, viscous liquid. Based on the stoichiometry of the reactants, 10 mol % of the total amine content in PEI 1200 was modified by reacting with 2-ethylhexyl glycidyl ether.

Preparatory Example 27: 2-Ethylhexyl glycidyl ether-Modified PEI 1200 (15 Mol % of amines in PEI Modified)

PEI 1200 (50 g, 1166.6 mmol of total amine content in PEI 1200) and 2-ethylhexyl glycidyl ether (32.6 g, 175 mmol) were added to a 250 mL round bottom flask. The mixture was stirred at 40° C. for 12 hours to give 2-ethylhexyl glycidyl ether-modified PEI as a colorless, viscous liquid. Based on the stoichiometry of the reactants, 15 mol % of the total amine content in PEI 1200 was modified by reacting with 2-ethylhexyl glycidyl ether.

Preparatory Example 28: 2-Ethylhexyl glycidyl ether-Modified PEI 600 (15 Mol % of amines in PEI Modified)

PEI 600 (50 g, 1166.6 mmol of total amine content in PEI 600) and 2-ethylhexyl glycidyl ether (32.6 g, 175 mmol) were added to a 250 mL round bottom flask. The mixture was stirred at 40° C. for 12 hours to give 2-ethylhexyl glycidyl ether-modified PEI as a colorless, viscous liquid. Based on the stoichiometry of the reactants, 15 mol % of the total amine content in PEI 600 was modified by reacting with 2-ethylhexyl glycidyl ether.

Preparatory Example 29: Dodecyl/tetradecyl glycidyl ether-Modified PEI 1200 (15 Mol % of amines in PEI Modified)

PEI 1200 (75 g, 1750 mmol of total amine content in PEI 1200) and dodecyl/tetradecyl glycidyl ether (67.3 g, 260 mmol) were added to a 250 mL round bottom flask. The mixture was stirred at 40° C. for 12 hours to give dodecyl/tetradecyl glycidyl ether-modified PEI as a colorless, viscous liquid. Based on the stoichiometry of the reactants, 15 mol % of the total amine content in PEI 1200 was modified by reacting with dodecyl/tetradecyl glycidyl ether.

Preparatory Example 30: Dodecyl/tetradecyl glycidyl ether-Modified PEI 600 (15 Mol % of amines in PEI Modified)

PEI 600 (75 g, 1750 mmol of total amine content in PEI 600) and dodecyl/tetradecyl glycidyl ether (32.6 g, 260 mmol) were added to a 250 mL round bottom flask. The mixture was stirred at 40° C. for 12 hours to give dodecyl/tetradecyl glycidyl ether-modified PEI as a colorless, viscous liquid. Based on the stoichiometry of the reactants, 15 mol % of the total amine content in PEI 600 was modified by reacting with dodecyl/tetradecyl glycidyl ether.

Preparatory Example 31: Glycidyl hexadecyl ether-Modified PEI 1200 (10 Mol % of amines in PEI Modified)

PEI 1200 (30 g, 700 mmol of total amine content in PEI 1200) and glycidyl hexadecyl ether (20.9 g, 70 mmol) were added to a 250 mL round bottom flask. The mixture was stirred at 40° C. for 12 hours to give glycidyl hexadecyl ether-modified PEI as a white solid. Based on the stoichiometry of the reactants, 10 mol % of the total amine content in PEI 1200 was modified by reacting with glycidyl hexadecyl ether.

Preparatory Example 32: Glycidyl hexadecyl ether-Modified PEI 1200 (15 Mol % of amines in PEI Modified)

PEI 1200 (30 g, 700 mmol of total amine content in PEI 1200) and glycidyl hexadecyl ether (31.3 g, 105 mmol) were added to a 250 mL round bottom flask. The mixture was stirred at 40° C. for 12 hours to give glycidyl hexadecyl ether-modified PEI as a white solid. Based on the stoichiometry of the reactants, 15 mol % of the total amine content in PEI 1200 was modified by reacting with glycidyl hexadecyl ether.

Preparatory Example 33: Glycidyl hexadecyl ether-Modified PEI 1200 (20 Mol % of amines in PEI Modified)

PEI 1200 (30 g, 700 mmol of total amine content in PEI 1200) and glycidyl hexadecyl ether (41.8 g, 140 mmol) were added to a 250 mL round bottom flask. The mixture was stirred at 40° C. for 12 hours to give glycidyl hexadecyl ether-modified PEI as a white solid. Based on the stoichiometry of the reactants, 20 mol % of the total amine content in PEI 1200 was modified by reacting with glycidyl hexadecyl ether.

Preparatory Example 34: Mixture of 2-ethylhexyl glycidyl ether-Modified PEI 1200 (15 Mol % of amines in PEI Modified) and 2-ethylhexyl glycidyl ether-Modified PEI 600 (15 Mol % of amines in PEI Modified)

2-Ethylhexyl glycidyl ether-modified PEI 1200 (15 mol % of amines in PEI modified, prepared according to Preparatory Example 27) was mixed 1:1 (volume/volume) with 2-ethylhexyl glycidyl ether-modified PEI 600 (15 mol % of amines in PEI modified, prepared according to Preparatory Example 28).

Viscosity Measurements of Preparatory Examples

Shear viscosity measurements of the Preparatory Examples for Parts A and B of curable compositions were determined using a TA Instruments AR-G2 Rheometer (TA Instruments, New Castle, DE) with a Peltier plate steel, 25 mm 5.739° cone plate. Samples are analyzed at 23° C. with a shear flow sweep at a rate ranging from 0.1/s to 100/s. The shear viscosity (Pascal-second) values are reported in Tables 3 and 4.

TABLE 3

Shear Viscosities of Part A Components

| Preparatory Example | Part A Component | Shear Viscosity Pascal-second (Pa-s) |
|---|---|---|
| 1 | Bis-oxamic acid ethyl ester of PRIAMINE 1075 | 14.3 |
| 2 | 2-Methylpentylene-bis-oxamic acid ethyl ester | 36.4 |
| 4 | Preparatory Example 1 + Hexanoic acid (10 weight %) | 5.2 |
| 5 | Preparatory Example 1 + Octanoic acid (5 weight %) | 7.7 |
| 6 | Preparatory Example 1 + Octanoic acid (2.5 weight %) | 8.4 |
| 7 | Preparatory Example 1 + Octanoic acid (1 weight %) | 10.3 |
| 8 | Preparatory Example 1 + 1-Octanol (2.5 weight %) | 8.5 |
| 9 | Preparatory Example 1 + 1,2-Octanediol (2.5 weight %) | 9.1 |
| 10 | Preparatory Example 1 + Decanoic acid (2.5 weight %) | 10.5 |
| 11 | Preparatory Example 1 + Decanoic acid (1 weight %) | 12.2 |
| 12 | Preparatory Example 1 + 2-Heptylundecanoic acid (2.5 weight %) | 10.3 |
| 13 | Preparatory Example 1 + 2-Heptylundecanoic acid (1 weight %) | 10.7 |
| 14 | Preparatory Example 1 + Isostearic acid (2.5 weight %) | 11.5 |
| 15 | Preparatory Example 1 + Isostearic acid (1 weight %) | 10.5 |
| 16 | Preparatory Example 1 + Oleic acid (2.5 weight %) | 9.9 |
| 17 | Preparatory Example 1 + Oleic acid (1 weight %) | 9.8 |

TABLE 4

Shear Viscosities of Part B Components

| Preparatory Example | Part B Component | Sheer Viscosity Pascal-second (Pa-s) |
|---|---|---|
| 18 | n-Butyl glycidyl ether-modified PEI 1200 (10 mol % of amines in PEI modified) | 16.4 |
| 19 | n-Butyl glycidyl ether-modified PEI 1200 (15 mol % of amines in PEI modified) | 24.9 |
| 20 | Octyl/decyl glycidyl ether-modified PEI 1200 (10 mol % of amines in PEI modified) | 21.0 |
| 21 | Octyl/decyl glycidyl ether-modified PEI 1200 (15 mol % of amines in PEI modified) | 15.4-22.8 |
| 22 | Octyl/decyl glycidyl ether-modified PEI 1200 (20 mol % of amines in PEI modified) | 27.7 |
| 23 | Octyl/decyl glycidyl ether-modified PEI 600 (10 mol % of amines in PEI modified) | 10.3 |
| 24 | Octyl/decyl glycidyl ether-modified PEI 600 (15 mol % of amines in PEI modified) | 13.2 |
| 25 | Octyl/decyl glycidyl ether-modified PEI 600 (20 mol % of amines in PEI modified) | 14.6 |
| 26 | 2-Ethylhexyl glycidyl ether-modified PEI 1200 (10 mol % of amines in PEI modified) | 14.9 |
| 27 | 2-Ethylhexyl glycidyl ether-modified PEI 1200 (15 mol % of amines in PEI modified) | 21.1 |
| 28 | 2-Ethylhexyl glycidyl ether-modified PEI 600 (15 mol % of amines in PEI modified) | 10.1 |
| 29 | Dodecyl/tetradecyl glycidyl ether-modified PEI 1200 (15 mol % of amines in PEI modified) | 23.8 |
| 30 | Dodecyl/tetradecyl glycidyl ether-modified PEI 600 (15 mol % of amines in PEI modified) | 9.8 |

Examples 1 to 4

Example 1. Cured Adhesive Compositions

Cured adhesive composition samples were prepared by first extruding the Part A and Part B components in a 1:1 volume/volume ratio using a double-barreled syringe with an in-line static mixer. The Part A component was loaded into one barrel and the Part B component was loaded into the other barrel. A 1 mL 3M Intra-oral syringe with a 4 mm tip (product no. 71506, 3M Company, St. Paul, MN) was used. A constant flow rate about 0.2-0.3 mL/second was maintained throughout the extrusion. The first 100 microliters of the mixed sample exiting the syringe tip was discarded to avoid possible artifacts at the flow front.

The resulting mixed composition was deposited into Teflon molds that contained individual rectangular wells measuring 50×10×0.125 mm. The wells were pre-treated with a thin coating of 3M Silicone Lubricant 08897 (3M Company) to facilitate release of the final adhesive composition from the wells. An excess volume of the mixed composition (typically 0.4-0.6 mL) was added to each well and the surface of the composition was smoothed using the edge of a razor blade. The individual wells were covered by a microscope glass slide that had been treated with a thin coating of 3M Silicone Lubricant 08897. The process was completed in less than 20 seconds so that the composition freely flowed during the mold filling.

The mixed composition was maintained for at least five minutes in order for curing of the composition to occur. The glass slide was removed, and the rectangular strips of the cured adhesive composition were removed from the mold. If any excess material was present along the edges, it was trimmed away using a razor blade.

Test samples for mechanical tensile testing were prepared from cured adhesive composition strips according to the following procedure. Each cured strip was placed on a sheet of silicone release liner (about 5.1×25.4 cm). Individual pieces of 3M Double Coated Urethane Foam Tape 4016 (3M Company) about 12.5 mm in length, were adhered to cover both the top and bottom surfaces at each end of the cured adhesive composition strip so that about 25 mm of the strip (in the lengthwise direction) remained uncovered between the foam tape sections. The surface of each foam section was subsequently covered with masking tape to improve gripping during tensile testing.

Tensile testing was performed in a testing chamber (30° C. and 25±5% humidity) using an Instron 6800 testing instrument (Instron Company, Norwood, MA) that was equipped with a 100 N load cell. The equipment and test samples were allowed to equilibrate in the test chamber for at least 30 minutes prior to testing.

Material characterization testing followed the guidelines of ASTM D882-18 (2018) 'Standard Test Method for Tensile Properties of Thin Plastic Sheeting'. The grip-to-grip separation was set to 25±1 mm, and the grips were attached to the foam sections of the test sample. Pretension of 0.05 N was applied, and the grips were pulled apart at the rate of 50 mm/minute until the point of failure. The travel distance and measured load were recorded. Failure was defined as test sample break or yield. Test results are reported in Table 5 as the average of six tests (n=6).

The Maximum Load was determined as the load cell reading at failure (reported in Newtons (N)).

Percent elongation of the cured adhesive composition was determined according to Equation A where L2 is the grip-to-grip separation distance at the point of failure or yield and L1 is the initial grip-to-grip separation distance.

$$\text{Percent elongation} = \frac{(L2 - L1)}{L1} \times 100\% \qquad \text{Equation A}$$

Tensile strength (M) of the cured adhesive composition was calculated as the tangent modulus at 10% elongation (Equation B). In Equation B, F10% is the load cell reading at 10% elongation; w is the width of the sample, and h is the thickness of the sample. Sample thickness was measured after the testing using a digital caliper to the nearest 0.01 mm.

$$M = \frac{F10\%}{w \times h} \qquad \text{Equation B}$$

TABLE 5

Cured Adhesive Compositions - Mechanical Properties

| Part A Component | Part B Component | Percent Elongation | Tensile Strength (MPa) | Maximum Load (N) |
|---|---|---|---|---|
| Preparatory Example 1 | Preparatory Example 28 | 65 ± 4 | 0.9 ± 0.1 | 0.6 ± 0.1 |
| Preparatory Example 1 | Preparatory Example 23 | 69 ± 16 | 1.9 ± 0.5 | 1.3 ± 0.4 |
| Preparatory Example 1 | Preparatory Example 24 | 61 ± 9 | 1.6 ± 0.5 | 1.0 ± 0.3 |
| Preparatory Example 1 | Preparatory Example 25 | 44 ± 7 | 2.7 ± 0.3 | 1.2 ± 0.3 |
| Preparatory Example 1 | Preparatory Example 27 | 34 ± 9 | 3.3 ± 0.3 | 1.3 ± 0.3 |
| Preparatory Example 1 | Preparatory Example 21 | 25 ± 6 | 2.8 ± 0.5 | 0.8 ± 0.2 |
| Preparatory Example 1 | Preparatory Example 29 | 29 ± 6 | 3.6 ± 0.3 | 1.2 ± 0.2 |
| Preparatory Example 1 | Preparatory Example 34 | 35 ± 6 | 1.1 ± 0.2 | 1.1 ± 0.2 |
| Preparatory Example 2 | Preparatory Example 27 | 32 ± 3 | 0.8 ± 0.2 | 0.6 ± 0.1 |

Example 2. Cure Time and Maximum Cure Temperature (Exotherm Temperature) Determination Part A and Part B components of a curable composition were extruded in a 1:1 volume/volume ratio using a double-barreled syringe with an in-line static mixer. The Part A component was loaded into one barrel and the Part B component was loaded into the other barrel. A 1 mL 3M Intra-oral syringe with a 4 mm tip (product no. 71506, 3M Company) was used. A constant flow rate about 0.2-0.3 mL/second was maintained throughout the extrusion. The first 100 microliters of the mixed sample exiting the syringe tip was discarded to avoid possible artifacts at the flow front. The remaining material was immediately extruded into a glass vial and an IKA 3378000 ETS-D5 Programmable Temperature Probe (IKA Works, Inc., Wilmington, NC) was immersed into the mixed composition. A timer was started as soon as the probe was immersed in the composition to record the time from immersion until the maximum temperature was reached. The maximum temperature was recorded as the Maximum Cure Temperature (Exotherm Temperature). The time to reach the maximum temperature was recorded as the Cure Time. The results are reported in Table 6 as the average of three tests (n=3).

TABLE 6

Cure Time and Maximum Cure Temperature

| Part A Component | Part B Component | Cure Time (seconds) | Maximum Cure Temperature (° C.) |
|---|---|---|---|
| Preparatory Example 1 | Preparatory Example 27 | 80 | 37.1 |
| Preparatory Example 17 | Preparatory Example 27 | 80 | 36.5 |
| Preparatory Example 13 | Preparatory Example 27 | 80 | 36 |

Example 3. Wound Closure Using Cured Adhesive Compositions

Wound closure samples were prepared according to ASTM F2458-05 (2015) 'Standard Test Method for Wound Closure Strength of Tissue Adhesives and Sealants' using skin from the backs or bellies of Yorkshire pigs. Freshly harvested skin was refrigerated at 4° C. and used within 10 days of collection or frozen at −20° C. If skin was previously frozen, it was allowed to thaw overnight at 4° C. the day before the testing. The fat layer was excised using a scalpel with #10 blade and the top epidermal layer was scraped off using 60 grit sandpaper.

Rectangular strips (25 mm in width and about 100 mm in length) were excised from the bulk skin and sequentially wrapped in gauze soaked in 1× phosphate saline buffer with 150 mM NaCl at pH 7.4; sealed in a plastic bag; and incubated for 60 minutes at 37° C. to rehydrate. Following rehydration, the skin strips were positioned on a non-slip surface with the fat layer facing down and dried by dabbing the skin surface with a low-lint wipe (KIMWIPES brand wipe, Kimberly-Clark Corporation, Irving, TX). Each skin strip was cut into two equal sections (25×50 mm) that were approximated along the cut line using forceps to create a wound interface that represented a surgical incision. The dermal area next to the wound interface was cleaned and degreased with neat isopropanol and allowed to dry. The curable composition (0.3-0.5 mL) was applied to the cleaned skin surfaces using the edge of a disposable razor blade. As applied, the curable composition was distributed to cover the entire incision and the skin surface of each section extending 5 mm from the incision line. The curable composition was allowed to cure for at least five minutes. Each skin sample was then gently re-wrapped in moist gauze, sealed in a plastic bag, and transferred into the testing chamber (maintained at 30° C. and the 25±5% humidity).

Wound closure testing was performed in the testing chamber using an Instron 6800 testing instrument that was equipped with a 100 N load cell per ASTM F2458-05 (2015). The equipment and test samples were allowed to equilibrate in the test chamber for at least 30 minutes prior to sample testing.

Sections at each end of the skin sample (each about 25.4 mm in length) were sandwiched between pieces of 60 grit sandpaper to enhance gripping and prevent slippage during testing. The grips of the Instron instrument were attached at the sandpaper sections and pulled apart in the direction perpendicular to the incision line at a rate of 50 mm/minute. Test data (travel distance and load) was collected when the load exceeded 0.5 N. The experiment was terminated when the wound closure integrity was violated (either through adhesive tearing or delamination of adhesive from skin) as evidenced by reduction of the measured load. The Maximum Load (described above) was determined from the recorded data and reported as the Wound Closure Strength (N). The wound closure strengths for the set of cured adhesive compositions tested are reported in Table 7 as the average of five tests (n–5). Skin samples from the bellies of Yorkshire pigs were used for all the tests.

TABLE 7

Wound Closure Strength of Cured Adhesive Compositions

| Components of the Cured Adhesive Compositions used in Example 3 | | Wound Closure Strength |
|---|---|---|
| Part A Component | Part B Component | (N) |
| Preparatory Example 1 | Preparatory Example 28 | 7.9 ± 2.6 |
| Preparatory Example 1 | Preparatory Example 27 | 5.7 ± 2.0 |

TABLE 7-continued

Wound Closure Strength of Cured Adhesive Compositions

| Components of the Cured Adhesive Compositions used in Example 3 | | Wound Closure Strength |
|---|---|---|
| Part A Component | Part B Component | (N) |
| Preparatory Example 3 | Preparatory Example 27 | 4.2 ± 1.8 |
| Preparatory Example 1 | Preparatory Example 26 | 4.1 ± 0.2 |

Example 4. Wound Closure Using Cured Adhesive Compositions

The same procedure as described in Example 3 was repeated with an additional set of cured adhesive compositions. The wound closure strengths are reported in Table 8 as the average of five tests (n–5). Skin samples from the backs of Yorkshire pigs were used for all of the tests.

TABLE 8

Wound Closure Strength of Cured Adhesive Compositions

| Components of the Cured Adhesive Compositions used in Example 4 | | Wound Closure Strength |
|---|---|---|
| Part A Component | Part B Component | (N) |
| Preparatory Example 1 | Preparatory Example 27 | 10.0 ± 1.4 |
| Preparatory Example 4 | Preparatory Example 27 | 7.5 ± 3.8 |
| Preparatory Example 5 | Preparatory Example 27 | 11.4 ± 3.0 |
| Preparatory Example 6 | Preparatory Example 27 | 10.7 ± 2.9 |
| Preparatory Example 7 | Preparatory Example 27 | 11.5 ± 2.3 |
| Preparatory Example 8 | Preparatory Example 27 | 9.9 ± 1.4 |
| Preparatory Example 9 | Preparatory Example 27 | 6.7 ± 3.5 |
| Preparatory Example 10 | Preparatory Example 27 | 8.1 ± 0.5 |
| Preparatory Example 11 | Preparatory Example 27 | 9.9 ± 2.9 |
| Preparatory Example 12 | Preparatory Example 27 | 7.0 ± 1.3 |
| Preparatory Example 13 | Preparatory Example 27 | 12.2 ± 2.0 |
| Preparatory Example 14 | Preparatory Example 27 | 11.1 ± 0.5 |
| Preparatory Example 15 | Preparatory Example 27 | 8.9 ± 4.3 |
| Preparatory Example 16 | Preparatory Example 27 | 11.3 ± 3.8 |
| Preparatory Example 17 | Preparatory Example 27 | 12.9 ± 3.0 |

What is claimed is:

1. A multiple-part curable composition comprising:
   a) a part A comprising an oxalamido-containing compound having a molecular weight of at least 250 grams/mole and having at least two oxalamido groups of formula —$NR^2$—(CO)—(CO)—$OR^1$,
   wherein
   $R^1$ is a hydrocarbyl; and
   $R^2$ is hydrogen or hydrocarbyl; and
   b) a part B comprising a derivatized polyethylene imine comprising a reaction product of a polyethylene imine with a glycidyl ether, the derivatized polyethylene imine comprising monomeric units of Formula (VI)

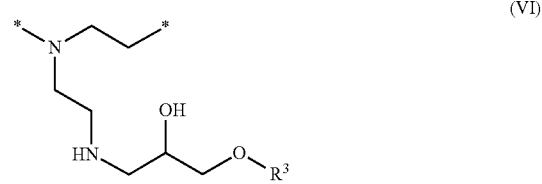

wherein
  R³ is an alkyl having at least 4 carbon atoms, an aryl, an aralkyl, or an alkaryl; and
  each asterisk (*) is an attachment site to another monomeric unit of the derivatized polyethylene imine.

2. The multiple-part curable composition of claim 1, wherein the oxalamido-containing compound is a compound of Formula (II)

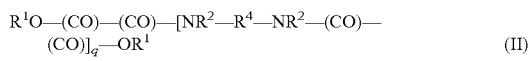

wherein
  R¹ is a hydrocarbyl;
  R² is hydrogen, or a hydrocarbyl; and
  R⁴ is a hydrocarbylene; and
  q is an integer in a range of 1 to 10.

3. The multiple-part curable composition of claim 2, wherein R⁴ is an alkylene, alkenylene, arylene, or a combination thereof.

4. The multiple-part curable composition of claim 1, wherein
  R¹ is alkyl, aryl, aralkyl, or alkaryl; and
  R² is hydrogen, alkyl, aryl, aralkyl, or alkaryl.

5. The multiple-part curable composition of claim 1, wherein the derivatized polyethylene imine further comprises monomeric units of Formula (V) and/or of Formula (VII)

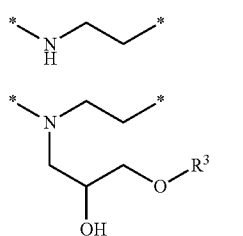

wherein
  R³ is an alkyl having at least 4 carbon atoms; and
  each asterisk (*) is an attachment site to another monomeric unit of the derivatized polyethylene imine.

6. The multiple-part curable composition of claim 1, wherein 10 to 25 mole percent of the monomeric units in the derivatized polyethylene imine are of Formula (VI) and/or Formula (VII)

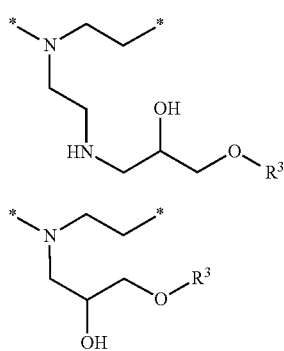

based on total moles of monomeric units in the derivatized polyethylene imine,
wherein
  R³ is an alkyl having at least 4 carbon atoms; and
  each asterisk (*) is an attachment site to another monomeric unit of the derivatized polyethylene imine.

7. The multiple-part curable composition of claim 1, wherein part A and/or part B further comprises a carboxylic acid having at least 4 carbon atoms.

8. The multiple-part curable composition of claim 7, wherein the carboxylic acid is a fatty acid.

9. The multiple-part curable composition of claim 7, wherein the carboxylic acid is in part A and in an amount of 0.01 to 10 weight percent based on a total weight of part A.

10. The multiple-part curable composition of claim 1, wherein part A has a first viscosity (V1) and part B has a second viscosity (V2) and wherein the second viscosity (V2) is in a range of 0.1(V1) to 10(V1).

11. The multiple-part curable composition of claim 1, wherein the molar ratio of primary amino groups in the derivatized polyethyleneimine of part B to oxalamido-containing compound in part A is in a range of 0.75 to 3.5.

12. A cured composition comprising a cured reaction product of a multiple-part curable composition of claim 1, wherein the cured composition is an adhesive.

13. The cured composition of claim 12, wherein the adhesive has a percent elongation at break that is in a range of 20 to 80 percent using ASTM method D882-2018 and/or has a closure strength of at least 2 Newtons using ASTM method F2458-05.

14. The cured composition of claim 12, wherein the adhesive is a tissue adhesive.

15. The cured composition of claim 12, wherein the adhesive is a wound closure adhesive.

16. A method of providing a cured composition, the method comprising:
  a) preparing or obtaining a part A composition comprising an oxalamido-containing compound having a molecular weight of at least 250 grams/mole and having at least two oxalamido groups of formula —NR²—(CO)—(CO)—OR¹,
  wherein
    R¹ is a hydrocarbyl; and
    R² is hydrogen or hydrocarbyl; and
  b) preparing or obtaining a part B composition comprising a derivatized polyethylene imine comprising a reaction product of a polyethylene imine with a glycidyl ether, the derivatized polyethylene imine having monomeric units of Formula (VI)

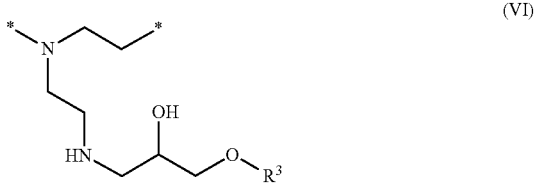

wherein
  R³ is an alkyl having at least 4 carbon atoms, an aryl, an aralkyl, or an alkaryl; and
  each asterisk (*) is an attachment site to another monomeric unit of the derivatized polyethylene imine;

c) combining part A with part B to form a reaction mixture; and d) curing the reaction mixture to form a cured composition that is an adhesive.

17. The method of claim 16, wherein combining part A with part B comprises placing part A and part B in separate syringes, dispensing part A and part B from the separate syringes, and combining part A with part B in a mixing chamber to form the reaction mixture.

18. The method of claim 17, further comprising discharging the reaction mixture from the mixing chamber prior to curing the reaction mixture.

19. The method of claim 18, wherein discharging comprises applying the reaction mixture to a tissue surface.

20. The method of claim 18, wherein discharging comprises applying the reaction mixture to an open wound to close the wound.

* * * * *